United States Patent
Hino et al.

(10) Patent No.: US 10,363,267 B2
(45) Date of Patent: Jul. 30, 2019

(54) DIARRHEA-PREVENTING NUTRITIONAL COMPOSITION

(71) Applicant: OTSUKA PHARMACEUTICAL FACTORY, INC., Naruto-shi, Tokushima (JP)

(72) Inventors: Kazuo Hino, Naruto (JP); Naoyuki Endo, Naruto (JP); Sho Miyatake, Naruto (JP)

(73) Assignee: OTSUKA PHARMACEUTICAL FACTORY, INC., Naruto-shi, Tokushima (JP)

( * ) Notice: Subject to any disclaimer, the term of this patent is extended or adjusted under 35 U.S.C. 154(b) by 0 days.

(21) Appl. No.: 16/308,701

(22) PCT Filed: Jun. 9, 2017

(86) PCT No.: PCT/JP2017/021424
§ 371 (c)(1),
(2) Date: Dec. 10, 2018

(87) PCT Pub. No.: WO2017/217326
PCT Pub. Date: Dec. 21, 2017

(65) Prior Publication Data
US 2019/0142862 A1    May 16, 2019

(30) Foreign Application Priority Data
Jun. 17, 2016 (JP) ................................ 2016-120988

(51) Int. Cl.
| | | |
|---|---|---|
| *A61K 31/732* | (2006.01) | |
| *A61K 31/715* | (2006.01) | |
| *A61K 38/17* | (2006.01) | |
| *A61K 36/899* | (2006.01) | |
| *A61P 3/02* | (2006.01) | |
| *A61K 33/42* | (2006.01) | |
| *A61K 31/716* | (2006.01) | |
| *A61P 1/12* | (2006.01) | |
| *A61K 9/08* | (2006.01) | |
| *A23L 33/16* | (2016.01) | |
| *A23L 33/125* | (2016.01) | |

(52) U.S. Cl.
CPC .......... *A61K 31/732* (2013.01); *A23L 33/125* (2016.08); *A23L 33/16* (2016.08); *A61K 9/08* (2013.01); *A61K 31/715* (2013.01); *A61K 31/716* (2013.01); *A61K 33/42* (2013.01); *A61K 36/899* (2013.01); *A61K 38/1709* (2013.01); *A61P 1/12* (2018.01); *A61P 3/02* (2018.01); *A23V 2002/00* (2013.01)

(58) Field of Classification Search
CPC ................ A61K 31/732; A61K 31/715; A61K 38/1709; A61K 36/899; A61K 33/42; A61K 31/716; A61K 9/08; A61P 3/02; A61P 1/12; A23L 33/16; A23L 33/125; A23V 2002/00
See application file for complete search history.

(56) References Cited

U.S. PATENT DOCUMENTS

| | | | |
|---|---|---|---|
| 4,950,655 A | 8/1990 | Bachmann | |
| 6,699,977 B1 | 3/2004 | Gerrish et al. | |
| 2009/0022871 A1* | 1/2009 | Thoegersen | A23L 29/231 426/577 |
| 2015/0045453 A1* | 2/2015 | Endo | A61K 9/107 514/777 |

FOREIGN PATENT DOCUMENTS

| | | |
|---|---|---|
| JP | 63-501216 A | 5/1988 |
| JP | 2004-503613 A | 2/2004 |
| JP | 2008-515445 A | 5/2008 |
| JP | 2013-253074 A | 12/2013 |

OTHER PUBLICATIONS

"Monitoring and countermeasure for preventing complications, Q14", In: Japanese Society for Parenteral & Enteral Nutrition (ed.), The third edition of Parenteral & Enteral Nutrition Guideline, SHORINSHA, 2013, pp. 166-167.

Alyce A. Schultz et al., "Effects of pectin on diarrhea in critically ill tube-fed patients receiving antibiotics", Am J Crit Care, Nov. 2000; pp. 403-411, vol. 9, No. 6.

Donna M. Zimmaro et al., "Isotonic tube feeding formula induces liquid stool in normal subjects: reversal by pectin", Journal of Parenteral and Enteral Nutrition, 1989, pp. 117-123, vol. 13, No. 2.

Shin'Ya Miki et al., "Hine E-gel no Kisoteki Kento [the 6th report]-Rat o Mochiita Geri Yokusei Koka no Kento-", The Journal of Japanese Society for Parenteral and Enteral Nutrition, 2015, p. 550, vol. 30, No. 1, P-1065.

Kazuyuki Yamaoka, "Keibi Keikan Eiyo Shiyo no Nyuin Geri Kanja ni Taishite Noko Ryudo Shokuhin Hine E-gel no Yuyosei ni tsuite", The Journal of Japanese Society for Parenteral and Enteral Nutrition, 2015, p. 453, vol. 30, No. 1, P-0680.

International Search Report of PCT/JP2017/021424 dated Jul. 18, 2017 [PCT/ISA/210].

* cited by examiner

*Primary Examiner* — Trevor Love
(74) *Attorney, Agent, or Firm* — Sughrue Mion, PLLC

(57) ABSTRACT

It is an object of the present invention to provide a nutritional composition for preventing diarrhea enabling ingestion or administration of nutritional ingredients while effectively preventing diarrhea, and is capable of stably keeping the viscosity when stored in a liquid form. A nutritional composition that is prepared by selecting a pectin having a degree of esterification of 10 to 30%, a degree of amidation of 0 to 25%, and a degree of free acids of 64% or more and less than 85% among pectins, and mixing the selected pectin with lipid, carbohydrate and protein, enables ingestion or administration of nutritional ingredients while effectively preventing diarrhea, and is capable of stably keeping the viscosity when stored in a liquid form.

19 Claims, No Drawings

DIARRHEA-PREVENTING NUTRITIONAL COMPOSITION

CROSS REFERENCE TO RELATED APPLICATIONS

This application is a National Stage of International Application No. PCT/JP2017/021424, filed Jun. 9, 2017, claiming priority based on Japanese Patent Application No. 2016-120988, filed Jun. 17, 2016.

TECHNICAL FIELD

The present invention relates to a nutritional composition for preventing diarrhea. More specifically, the present invention relates to a nutritional composition for preventing diarrhea that enables ingestion or administration of nutritional ingredients while effectively preventing diarrhea, and is capable of stably keeping the viscosity when stored in a liquid form.

BACKGROUND ART

Patients suffering from brain damage such as a stroke, and elderly people have depressed swallowing functions, and often suffer from dysphagia which is a malfunction that food erroneously flows into the trachea or the lung at the time of taking the food. As one method for nutritional supplementation for such people suffering from dysphagia, a tube feeding method for directly administering a liquid diet into the stomach by means of a tube is known. In a patient undergoing the tube feeding, diarrhea is the symptom that is most frequently observed. In a patient undergoing the tube feeding, sufficient attention should be given for the composition of the enteral nutrient, the temperature of the administered nutrient, and the administration speed so as to prevent diarrhea (see Non-Patent Document 1).

It has been conventionally reported that among dietary fibers to be mixed in an enteral nutrient, pectin has a diarrhea-preventing effect (see Non-Patent Document 2). However, it has been also revealed that clear diarrhea-preventing effect is not necessarily exerted only by selecting pectin as the dietary fiber to be mixed in the enteral nutrient (see Non-Patent Document 3).

It has been also reported that low methoxyl pectin having a degree of esterification of 5 to 15% and a viscosity-average molecular weight of 10000 to 35000 can be used as an active ingredient of a diarrhea-preventing agent in enterally administering a nutrient directly to the small intestine without passing through the stomach (see Patent Document 1). However, it is the current state of the art that sufficient diarrhea-preventing effect has not yet been achieved even with the pectin having a structure disclosed in Patent Document 1. Further, since the diarrhea-preventing agent of Patent Document 1 is administered separately from a nutrient, a great burden is imposed on a carer, and if administration is missed, the diarrhea-preventing effect is not obtained, and also there is a drawback that versatility is poor because administration thereof is limited to direct administration to the small intestine.

Meanwhile, pectin is polysaccharide mainly extracted from a pericarp of citrus such as lemon, and is known to have a structure of a linear polysaccharide having a main structure of D-galacturonic acids linked by α-1,4-bonds. Pectin in a cell wall of a plant exists in the state that carboxyl groups of D-galacturonic acids are methyl-esterified with high frequency. The nature of pectin varies depending on the degree of esterification (the ratio of methyl-esterified galacturonic acids: DE value), and pectin is classified into high methoxyl pectin having a degree of esterification of 50% or more and low methoxyl pectin having a degree of esterification of less than 50%. Also, a carboxyl group can be amidated depending on the purification and de-esterification step of pectin. It is known that the degree of esterification and the degree of amidation of pectin (DA value) influence on the gelation characteristics of pectin. However, the mechanism of preventing diarrhea by pectin has not been well elucidated, and whether the difference in structure of pectin leads difference in the diarrhea preventing effect has not been clarified yet.

In addition, nutrients need to stably keep the physical properties during storage, and in particular, enteral nutrients are required to have appropriate viscosity at the time of administration from the view point of easiness of administration, and it is particularly important to stably keep appropriate viscosity during storage. However, for pectins to be conventionally mixed in the nutrient, the relation between the structure of the pectin and the viscosity stability during storage has not been examined so far.

PRIOR ART DOCUMENTS

Non-Patent Document

Non-Patent Document 1: Monitoring and countermeasure for preventing complications, Q14. In: Japanese Society for Parenteral & Enteral Nutrition (ed.), The third edition of Parenteral & Enteral Nutrition Guideline, SHORIN-SHA, 2013, p. 166-167.

Non-Patent Document 3: Schultz A A, Ashby-Hughes B, Taylor R, Gillis D E, Wilkins M. Effects of pectin on diarrhea in critically ill tube-fed patients receiving antibiotics. Am J Crit Care. 2000; 9(6): 403-11.

Non-Patent Document 2: Zimmaro D M, Rolandelli R H, Koruda M J, Settle R G, Stein T P, Rombeau J L. Isotonic tube feeding formula induces liquid stool in normal subjects: reversal by pectin. JPEN J Parenter Enteral Nutr. 1989; 13(2): 117-23.

Patent Documents

Patent Document 1: Japanese Patent Laid-open Publication No. 2013-253074

SUMMARY OF THE INVENTION

Problems to be Solved by the Invention

It is an object of the present invention to provide a nutritional composition for preventing diarrhea that enables ingestion or administration of nutritional ingredients while effectively preventing diarrhea, and is capable of stably keeping the viscosity when stored in a liquid form.

Means for Solving the Problem

The present inventors made diligent efforts to solve the above problems, and found that a nutritional composition that is prepared by selecting a pectin having a degree of esterification of 10 to 30%, a degree of amidation of 0 to 25%, and a degree of free acids of 64% or more and less than 85% among pectins, and mixing the selected pectin with lipid, carbohydrate and protein, enables ingestion or administration of nutritional ingredients while effectively preventing diarrhea, and is capable of stably keeping the viscosity when stored in a liquid form. The present invention was accomplished by further repeating examinations on the basis of such findings.

That is, the present invention provides the invention of the following aspects.

Item 1. A nutritional composition for preventing diarrhea comprising
a pectin having a degree of esterification of 10 to 30%, a degree of amidation of 0 to 25%, and a degree of free acids of 64% or more and less than 85%,
lipid,
carbohydrate other than the pectin, and
protein.

Item 2. The nutritional composition for preventing diarrhea according to item 1, wherein the pectin has a weight-average molecular weight of 350000 to 600000.

Item 3. The nutritional composition for preventing diarrhea according to item 1 or 2, wherein as the carbohydrate, dietary fiber other than the pectin, and/or saccharide is contained.

Item 4. The nutritional composition for preventing diarrhea according to any one of items 1 to 3, wherein as the carbohydrate, gum arabic and/or ghatti gum is contained.

Item 5. The nutritional composition for preventing diarrhea according to any one of items 1 to 4, further comprising a bivalent metal salt.

Item 6. The nutritional composition for preventing diarrhea according to item 5, wherein the bivalent metal salt is an insoluble salt that releases a bivalent metal ion in an acidic region.

Item 7. The nutritional composition for preventing diarrhea according to any one of items 1 to 6, which is in a liquid form.

Item 8. The nutritional composition for preventing diarrhea according to item 7, containing 3 to 15 g/L of the pectin.

Item 9. The nutritional composition for preventing diarrhea according to item 7 or 8, having a viscosity at 25° C. of 2 to 100 mPa·s.

Item 10. Use of a composition comprising a pectin having a degree of esterification of 10 to 30%, a degree of amidation of 0 to 25%, and a degree of free acids of 64% or more and less than 85%, lipid, carbohydrate other than the pectin, and protein, for the manufacture of a nutritional composition for preventing diarrhea.

Item 11. A method for preventing diarrhea, comprising the step of making a subject in need of preventing diarrhea have administration or ingestion with the nutritional composition for preventing diarrhea according to any one of items 1 to 9.

Effects of the Invention

The nutritional composition for preventing diarrhea of the present invention enables ingestion or administration of nutritional ingredients while effectively preventing diarrhea. Further, since the nutritional composition for preventing diarrhea of the present invention is capable of stably keeping the viscosity even when it is stored in a liquid form, the appropriate viscosity that is suited for ingestion or administration can be stably kept until use.

DESCRIPTION OF EMBODIMENTS

The nutritional composition for preventing diarrhea of the present invention includes a pectin having a degree of esterification of 10 to 30%, a degree of amidation of 0 to 25%, and a degree of free acids of 64% or more and less than 85%, lipid, carbohydrate other than the pectin, and protein. The nutritional composition for preventing diarrhea of the present invention is provided in a liquid form, and can be directly ingested or administered for prevention of diarrhea and for nutrition. Also, the nutritional composition for preventing diarrhea of the present invention can be provided in a solid form (powder form, granular form), and can be ingested or administered for preventing diarrhea or for nutrition after it is prepared into a liquid form by addition of water. Hereinafter, the nutritional composition for preventing diarrhea of the present invention is specifically described.

In this context, the expression "X to Y" for a numerical range means X or more and Y or less.

[Pectin]

In the nutritional composition for preventing diarrhea of the present invention, a pectin having a degree of esterification of 10 to 30%, a degree of amidation of 0 to 25%, and a degree of free acids of 64% or more and less than 85% is used. By selecting the pectin having such a specific structure, it becomes possible to exert excellent diarrhea preventing effect. Further, the pectin is capable of providing the nutritional composition for preventing diarrhea of the present invention with a viscosity suited for enteral administration, and providing the nutritional composition for preventing diarrhea of the present invention with viscosity stability even in storage in a liquid form. Further, the pectin has characteristics of gelating in an acidic region in the presence of a bivalent metal salt. Therefore, when a bivalent metal salt is mixed in the nutritional composition for preventing diarrhea of the present invention, the composition has appropriate fluidity in the liquid form at the time of ingestion or administration, but gelates after the entry into the stomach. Therefore, gastroesophageal reflux can be prevented.

The degree of esterification of pectin means a percentage of galacturonic acid residues existing in the form of a methyl ester among all the D-galacturonic acid resins constituting the pectin. The pectin used in the present invention can have a degree of esterification of 10 to 30%, and from the view point of preventing diarrhea more effectively, the degree of esterification is preferably 10 to 25%.

The degree of amidation of pectin means a percentage of galacturonic acid residues having an amide group among all the D-galacturonic acid resins constituting the pectin. The pectin used in the present invention can have a degree of amidation of 0 to 25%, and from the view point of improving the stability during storage while preventing diarrhea more effectively, the degree of amidation is preferably 15 to 21%.

The degree of free acids of pectin is also called a free acid content or a DFA value, and is a value calculated by 100%−(degree of esterification+degree of amidation). The pectin used in the present invention can have a degree of free acids of 64% or more and less than 85%, and from the view point of improving the stability during storage while preventing diarrhea more effectively, the degree of free acids is preferably 64 to 80%.

In the present invention, the degree of esterification, the degree of amidation, and the degree of free acids of pectin are values measured in accordance with the pectin purity test method described in "Japan's Specifications and Standards for Food Additives, the eighth edition, the reprinted edition of reprinted by the Ministry of Health and Welfare" (published by Japan Food Additives Association, published on Aug. 31, 2007). Concrete conditions for measuring the degree of esterification, the degree of amidation, and the degree of free acids of pectin are as follows.

(Conditions for Measuring Degree of Esterification, Degree of Amidation, and Degree of Free Acids)

About 5 g of a sample is precisely weighed, and put into a beaker, and 5 ml of hydrochloric acid and 100 ml of 60 vol % ethanol are added, and then mixed for 10 minutes, and then filtered with a glass filter (1G3), and the residue is washed six times with 15 ml of 60 vol % ethanol/hydrochloric acid mixture (20:1). Then the residue on the glass filter is washed with 60 vol % ethanol until the washings no longer exhibit the reaction of hydrochloride. The residue is further washed with 20 ml of ethanol, dried at 105° C. for 2.5 hours, and cooled, and then the weight is measured. The amount corresponding to about one-tenth of this is precisely measured, and the measured mass is referred to as W (mg). This portion is moisturized by addition of 2 ml of ethanol, and then 100 ml of water that has been boiled and cooled is added, and hydrated by sometimes mixing by shaking. Then five drops of a phenolphthalein solution are added, and titration with a 0.1 mol/L sodium hydroxide solution is carried out to give a titration value of $V_1$. Then 20 ml of a 0.5 mol/L sodium hydroxide solution is accurately measured and added, and well mixed by shaking, and left still for 15 minutes. Further, 20 ml of 0.5 mol/L hydrochloric acid is accurately measured and added, and mixed by shaking until the pink of the liquid disappears, and titration with a 0.1 mol/L sodium hydroxide solution is carried out to give a titration value of $V_2$. When the liquid shows slightly pink by vigorous shaking, the point of time is regarded as an end point. According to the apparatus of the Kjeldahl method in the nitrogen determination, the titrated liquid is transferred to a 500 ml separation flask, and a spray strip and a condenser are attached to the flask. A flask for absorption is charged in advance with 20 ml of 0.1 mol/L hydrochloric acid and 150 ml of water that has been newly boiled and cooled, and the lower end of the condenser is dipped in this liquid. The separation flask is charged with 20 ml of sodium hydroxide (1→10) solution, and heated with care not to cause too much bubbling to carry out distillation until 80 to 120 ml is distilled out. Several drops of a methyl red test solution were added, and titration with a 0.1 mol/L sodium hydroxide solution is carried out to give a titration value of S. Separately, a blank test is carried out to give a titration value of B. Then, according to the following formulas, degree of esterification, degree of amidation, and degree of free acids are calculated.

[Numerical formula 1]

Degree of esterification =
$$\frac{V_2}{V_1 + V_2 + (B - S)} \times 100(\%)$$

Degree of amidation =
$$\frac{(B - S)}{V_1 + V_2 + (B - S)} \times 100(\%)$$

Degree of free acids =
$$\frac{V_1}{V_1 + V_2 + (B - S)} \times 100(\%)$$

The weight-average molecular weight of the pectin used in the present invention is, for example, but not particularly limited to, 350000 to 600000, preferably 400000 to 530000, more preferably 400000 to 510000. Here, the weight-average molecular weight of the pectin is a value measured by size exclusion chromatography using maltotriose and pullulan reference standards as standard substances.

In the nutritional composition for preventing diarrhea of the present invention, the content of the pectin having the aforementioned structure can be appropriately selected depending on the form of the nutritional composition for preventing diarrhea, and an amount of ingestion or administration per one time, and is for example, 3 to 15 g/L, preferably 5 to 10 g/L, more preferably 6 to 8 g/L when the nutritional composition for preventing diarrhea is provided in a liquid form. In the case where the nutritional composition for preventing diarrhea of the present invention is provided in a solid form, the content of the pectin having the aforementioned structure in the solid nutritional composition for preventing diarrhea can be appropriately selected so that the content of the pectin having the aforementioned structure falls within the above range when the solid nutritional composition for preventing diarrhea is made into a liquid by addition of a predetermined amount of water before ingestion or administration.

[Lipid]

The nutritional composition for preventing diarrhea of the present invention contains lipid as a nutritional ingredient.

Examples of the lipid used in the present invention include, but are not particularly limited to, vegetable oils such as rice bran oil, coconut oil, soybean oil, corn oil, rapeseed oil, palm oil, safflower oil, sunflower oil, soybean oil, olive oil, cottonseed oil, peanut oil, and cacao oil; animal oils such as fish oil, beef tallow, and lard; fatty acid, medium-chain fatty acid (having about 6 to 12 carbon atoms) triglyceride, docosahexaenoic acid, and eicosapentaenoic acid. These lipids may be used singly or in combination of two or more kinds.

In the nutritional composition for preventing diarrhea of the present invention, it is preferred that the lipid is contained in an emulsified state when the nutritional composition for preventing diarrhea is made into a liquid form. When the lipid is contained in the nutritional composition for preventing diarrhea of the present invention and emulsified, the emulsion form is not particularly limited, and may be an oil in water emulsion or a water in oil emulsion, with the oil in water emulsion being preferred. When the nutritional composition for preventing diarrhea of the present invention is provided in a solid form, solid fats and oils are preferably used as fats and oils.

The content of lipid in the nutritional composition for preventing diarrhea of the present invention can be appropriately selected depending on the kind of the lipid to be used and the energy density or the like to be provided, and a total amount of lipid is for example, 0.1 to 100 g/L, preferably 5 to 70 g/L, more preferably 10 to 40 g/L when the nutritional composition for preventing diarrhea is provided in a liquid form. Further, in the case where the nutritional composition for preventing diarrhea of the present invention is provided in a solid form, the content of lipid in the solid nutritional composition for preventing diarrhea can be appropriately selected so that the content of lipid falls within the above range when the solid nutritional composition for preventing diarrhea is made into a liquid by addition of a predetermined amount of water before ingestion or administration.

[Carbohydrate]

The nutritional composition for preventing diarrhea of the present invention contains carbohydrate other than the pectin as a nutritional ingredient.

Examples of the carbohydrate used in the present invention include, but are not particularly limited to, dietary fiber other than the pectin, and saccharide. These carbohydrates may be used singly or in combination of two or more kinds.

Concrete examples of the dietary fiber other than the pectin include low methoxyl pectins other than the pectin having the aforementioned structure, high methoxyl pectins, alginic acid, salts of alginic acid (alkali metal salts such as a potassium salt, and a sodium salt), gellan gum, carageenan, gum arabic, and ghatti gum. Among these dietary fibers, gum arabic, and ghatti gum are preferred, and ghatti gum is more preferred. These dietary fibers may be used singly or in combination of two or more kinds.

Concrete examples of the saccharide include monosaccharides such as glucose, galactose, fructose, and xylose; disaccharides such as sucrose, lactose, and maltose; oligosaccharides such as galacto-origosaccharide, xylo-origosaccharide, soybean origosaccharide, fructo-origosaccharide, and lactosucrose, and polysaccharides such as dextrin and starch. These saccharides may be used singly or in combination of two or more kinds.

The content of carbohydrate in the nutritional composition for preventing diarrhea of the present invention can be appropriately selected depending on the kind of the carbohydrate to be used and the energy density or the like to be provided, and a total amount of carbohydrate is for example, 3 to 300 g/L, preferably 3 to 200 g/L, more preferably 3 to 180 g/L when the nutritional composition for preventing diarrhea is provided in a liquid form. Further, in the case where the nutritional composition for preventing diarrhea of the present invention is provided in a solid form, the content of carbohydrate in the solid nutritional composition for preventing diarrhea can be appropriately selected so that the content of carbohydrate falls within the above range when the solid nutritional composition for preventing diarrhea is made into a liquid by addition of a predetermined amount of water before ingestion or administration.

Concretely, when dietary fiber other than the pectin having the aforementioned structure is used, and the nutritional composition for preventing diarrhea is in a liquid form, a total amount of the dietary other than the pectin having the aforementioned structure is for example, 3 to 100 g/L, preferably 3 to 80 g/L, more preferably 3 to 60 g/L. More concretely, when gum arabic is used, and the nutritional composition for preventing diarrhea is provided in a liquid form, the content of gum arabic in the nutritional composition for preventing diarrhea is for example, 20 to 70 g/L, preferably 30 to 60 g/L, more preferably 40 to 50 g/L. When ghatti gum is used, and the nutritional composition for preventing diarrhea is provided in a liquid form, the content of ghatti gum in the nutritional composition for preventing diarrhea is for example, 0.5 to 20 g/L, preferably 0.5 to 15 g/L, more preferably 3 to 10 g/L, particularly preferably 3 to 7.5 g/L. In the case where the nutritional composition for preventing diarrhea of the present invention is provided in a solid form, a total amount of dietary fiber, a content of gum arabic, and a content of ghatti gum can be appropriately selected in the nutritional composition for preventing diarrhea so that these contents fall within the above ranges when the solid nutritional composition for preventing diarrhea is made into a liquid by addition of a predetermined amount of water before ingestion or administration.

When saccharide is used, and the nutritional composition for preventing diarrhea of the present invention is provided in a liquid form, the content of saccharide in the nutritional composition for preventing diarrhea can be a total amount of saccharide of, for example, 3 to 300 g/L, preferably 3 to 200 g/L, and more preferably 3 to 180 g/L. Further, in the case where the nutritional composition for preventing diarrhea of the present invention is provided in a solid form, the content of saccharide in the solid nutritional composition for preventing diarrhea can be appropriately selected so that the content of saccharide falls within the above range when the solid nutritional composition for preventing diarrhea is made into a liquid by addition of a predetermined amount of water before ingestion or administration.

[Protein]

The nutritional composition for preventing diarrhea of the present invention contains protein as a nutritional ingredient.

While the origin of the protein used in the present invention is not particularly limited, for example, proteins derived from vegetables, such as soybean, wheat, pea and rice; and proteins derived from animals such as egg, fish, meat, milk and collagen can be recited. These proteins may be low molecular weight molecules digested by enzymolysis or the like. These proteins may be used singly or in combination of two or more kinds.

The content of protein in the nutritional composition for preventing diarrhea of the present invention can be appropriately selected depending on the kind of the protein to be used, and is for example, 5 to 100 g/L, preferably 10 to 80 g/L, more preferably 30 to 70 g/L, when the nutritional composition for preventing diarrhea is provided in a liquid form. In the case where the nutritional composition for preventing diarrhea of the present invention is provided in a solid form, the content of protein in the solid nutritional composition for preventing diarrhea can be appropriately selected so that the content of protein falls within the above range when the solid nutritional composition for preventing diarrhea is made into a liquid by addition of a predetermined amount of water before ingestion or administration.

[Water]

The nutritional composition for preventing diarrhea of the present invention contains water as a base material when the composition is provided in a liquid form. When the nutritional composition for preventing diarrhea of the present invention is provided in a solid form, the composition is made into a liquid form by addition of water before ingestion or administration so as to facilitate the ingestion or the administration.

When the nutritional composition for preventing diarrhea of the present invention is provided in a liquid form, the content of water can be appropriately selected depending on the viscosity to be exhibited or the like, and the content of water is for example, 500 to 990 g/L, preferably 600 to 950 g/L, more preferably 700 to 900 g/L. In the case where the nutritional composition for preventing diarrhea of the present invention is provided in a solid form, water can be added so that the content of water falls within the aforementioned range, and mixed them to make the nutritional composition for preventing diarrhea into a liquid form before ingestion or administration.

[Bivalent Metal Salt]

It is desired that the nutritional composition for preventing diarrhea of the present invention contains a bivalent metal salt. Since the pectin having the aforementioned specific structure has characteristics of gelating in an acidic region in the presence of a bivalent metal salt, the nutritional composition for preventing diarrhea of the present invention containing a bivalent metal salt has appropriate fluidity in the liquid form at the time of ingestion or administration, and becomes possible to prevent gastroesophageal reflux by promoting gelation of the pectin when it enters the stomach and is exposed to an acidic environment.

Concrete examples of the bivalent metal that constitutes the bivalent metal salt include magnesium, calcium and barium. Among these, magnesium and calcium are preferred.

The bivalent metal salt used in the present invention is preferably an insoluble salt that releases a bivalent metal ion in an acidic region since bivalent metal ions promote thickening and gelation of the pectin having a specific structure. Here, the "insoluble salt that releases a bivalent metal ion in an acidic region" refers to those showing insolubility or difficult solubility in a neutral to basic region, but dissolve to release a bivalent metal ion in an acidic region. Also, the "insolubility" means requiring 10,000 g or more of water to dissolve 1 g of the sample, and "difficult solubility" means requiring 1,000 to 10,000 g of water to dissolve 1 g of the sample. By using an insoluble salt that releases a bivalent metal ion in an acidic region as the bivalent metal salt, it becomes possible to promote thickening of the thickener or gelation in association with reduction in pH at the time of entry into the stomach while disabling promotion of the thickening or the gelation during distribution and storage. Examples of the insoluble salt that releases a bivalent metal ion in an acidic region include phosphates of bivalent metal such as tricalcium phosphate and trimagnesium phosphate; oxides of bivalent metal such as calcium oxide and magnesium oxide; and carbonates of bivalent metal such as calcium carbonate and magnesium carbonate. Among these, phosphates of bivalent metal are preferred.

The bivalent metal salt may be chlorides of bivalent metal, sulfates of bivalent metal, bivalent metal salts of organic acid and the like as long as they are designed not to release a bivalent metal ion in a neutral region but release a bivalent metal ion at acidic pH by conducting gastrosoluble coating, or forming a soluble complex ion by being used in combination with orthophosphate, polymerized phosphate or the like.

These bivalent metal salts may be used singly or in combination of two or more kinds.

Among these bivalent metal salts, from the view point of effectively providing the characteristics of gelating in the stomach, phosphates of bivalent metal, oxides of bivalent metal, and carbonates of bivalent metal are preferred; phosphates of bivalent metal are more preferred, and calcium phosphate and magnesium phosphate are particularly preferred.

The content of the bivalent metal salt in the nutritional composition for preventing diarrhea of the present invention can be appropriately selected depending on the kind of the bivalent metal salt to be used, and is for example, 0.1 to 10 g/L, preferably 0.5 to 7 g/L, more preferably 1 to 5 g/L, when the nutritional composition for preventing diarrhea is provided in a liquid form. In the case where the nutritional composition for preventing diarrhea of the present invention is provided in a solid form, the content of the bivalent metal salt in the solid nutritional composition for preventing diarrhea can be appropriately selected so that the content of the bivalent metal salt falls within the above range when the solid nutritional composition for preventing diarrhea is made into a liquid by addition of a predetermined amount of water before ingestion or administration.

[Other Ingredients]

The nutritional composition for preventing diarrhea of the present invention may further contain additives including an emulsifier such as lecithin, sucrose fatty acid ester, glycerin fatty acid ester, or sorbitan fatty acid ester, a pH adjustor, vitamins, minerals, a sweetener, an antioxidant, an antiseptic, a seasoning, a coloring agent, and a flavor as necessary.

[Physical Properties of Nutritional Composition for Preventing Diarrhea]

When the nutritional composition for preventing diarrhea of the present invention is provided in a liquid form, the pH is typically 5.5 or more and less than 9, preferably 6.0 to 8.0, from the view point of retaining excellent viscosity while preventing gelation and thickening during distribution and storage. Further, in the case where the nutritional composition for preventing diarrhea of the present invention is provided in a solid form, the composition in the solid nutritional composition for preventing diarrhea can be appropriately selected so that the pH falls within the above range when the solid nutritional composition for preventing diarrhea is made into a liquid by addition of a predetermined amount of water before ingestion or administration.

When the nutritional composition for preventing diarrhea of the present invention is provided in a liquid form, the viscosity is typically 2 to 100 mPa·s, preferably 3 to 70 mPa·s, more preferably 5 to 50 mPa·s. Such viscosity gives excellent fluidity and facilitates administration by means of a gastrostomy tube or a nasotracheal tube. Further, since the nutritional composition for preventing diarrhea of the present invention is also provided with viscosity stability during storage in a liquid form, it is possible to prevent the viscosity from increasing during storage, and to stably keep the viscosity range as described above. The viscosity is a value measured at 25° C. using a type B viscometer and an L adaptor at a number of rotations of 12 rpm.

Further, in the case where the nutritional composition for preventing diarrhea of the present invention is provided in a solid form, the composition in the solid nutritional composition for preventing diarrhea can be appropriately selected so that the viscosity falls within the above range when the solid nutritional composition for preventing diarrhea is made into a liquid by addition of a predetermined amount of water before ingestion or administration.

In order to provide the nutritional composition for preventing diarrhea of the present invention with the aforementioned viscosity, the content of the aforementioned pectin having a specific structure, kinds and contents of the nutritional ingredients, and the like can be adjusted.

The energy density of the nutritional composition for preventing diarrhea of the present invention is not particularly limited, and can be appropriately selected, and when the nutritional composition for preventing diarrhea is provided in a liquid form, the energy density is for example, 0.1 to 7 kcal/g, preferably 0.3 to 5 kcal/g, more preferably 0.5 to 3 kcal/g. Further, in the case where the nutritional composition for preventing diarrhea of the present invention is provided in a solid form, the composition in the solid nutritional composition for preventing diarrhea can be appropriately selected so that the energy density falls within the above range when the solid nutritional composition for preventing diarrhea is made into a liquid by addition of a predetermined amount of water before ingestion or administration.

[Form of Nutritional Composition for Preventing Diarrhea]

As described above, the nutritional composition for preventing diarrhea of the present invention may be provided in a liquid form, or may be provided in a solid form such as a powder form or a granular form.

When the nutritional composition for preventing diarrhea of the present invention is in a liquid form, it is possible to stably keep the viscosity during storage.

When the nutritional composition for preventing diarrhea of the present invention is in a solid form, water is added to the nutritional composition for preventing diarrhea before ingestion or administration. In the case of a solid form, an amount for a plurality of times of ingestion or administration of the nutritional composition for preventing diarrhea can be prepared at once and stored because the viscosity can be stably kept even when the nutritional composition for preventing diarrhea is made into a liquid form by addition of water and stored in the liquid form.

[Method for Producing Nutritional Composition for Preventing Diarrhea]

The nutritional composition for preventing diarrhea of the present invention is prepared in a production method suited for its form. For example, when the nutritional composition for preventing diarrhea of the present invention is in a liquid form, the nutritional composition for preventing diarrhea can be produced by adding predetermined amounts of the aforementioned pectin having a specific structure, lipid, carbohydrate, protein and other ingredient to be mixed as necessary, to water, and mixing them. For making the nutritional composition for preventing diarrhea of the present invention into an emulsified form, water can be mixed into the mixture and emulsified with a homogenizer. When a bivalent metal salt is mixed with the nutritional composition for preventing diarrhea of the present invention, it is desired that the mixture to which the bivalent metal salt is to be added is prepared to have a pH region where the aforementioned pectin having a specific structure does not gelate by the bivalent metal salt at the time of addition of the bivalent metal salt.

When the nutritional composition for preventing diarrhea of the present invention is provided in a liquid form, it is preferred that the nutritional composition for preventing diarrhea is subjected to a heat sterilization treatment before or after it is packed in a container such as an aluminum pouch or a soft bag. Such a heat sterilization treatment can heighten the storage stability. The temperature condition of the heat sterilization treatment is for example, but not particularly limited to, 110 to 150° C., preferably 120 to 145° C. Concrete examples of the heat sterilization treatment include pressure heat sterilization, momentary ultra-high-temperature sterilization (UHT) and high-temperature short time sterilization (HTST).

Also, when the nutritional composition for preventing diarrhea of the present invention is provided in a solid form, the nutritional composition for preventing diarrhea can be produced by adding predetermined amounts of the aforementioned pectin having a specific structure, lipid, carbohydrate, protein and other ingredient to be mixed as necessary, and mixing them. Also, after adding the predetermined amounts of the components to water and mixing them, the mixture may be prepared into a powder form or a granular form by spray drying, freeze-drying, fluidized bed drying, vacuum drying or the like, or may be prepared into a granular form by being subjected to a fluidized-bed granulation, fluidized-bed multifunctional granulation, spray-drying granulation, oscillating granulation, stirring granulation or the like.

[Applications and Usage of Nutritional Composition for Preventing Diarrhea]

The nutritional composition for preventing diarrhea of the present invention is used for the purpose of amelioration or prophylaxis of diarrhea, and for the purpose of nutrition. The subject to which the nutritional composition for preventing diarrhea of the present invention is applied can be a subject having a symptom of diarrhea and being in need of amelioration thereof, or a subject having a risk of developing diarrhea and being in need of prevention thereof. In particular, a patient undergoing the tube feeding frequently suffers from diarrhea, and is suited as a subject to which the nutritional composition for preventing diarrhea of the present invention is applied.

The method for ingesting or administering the nutritional composition for preventing diarrhea of the present invention may be any method as long as the nutritional composition for preventing diarrhea is ingested or administered in a liquid form. For example, for use for a person without dysphagia, ingestion is recited, and for use for a person having dysphagia, enteral administration by means of a gastrostomy tube (catheter), a nasotracheal tube (catheter) or the like is recited.

While the amount of ingestion or administration of the nutritional composition for preventing diarrhea of the present invention is appropriately selected depending on the energy density thereof, the symptom, sex, age and the like of the subject of the ingestion or administration, an amount of ingestion or administration of the nutritional composition for preventing diarrhea of the present invention per one time is about 3 to 18 g, preferably 7 to 12 g in terms of the amount of the aforementioned pectin having a specific structure, one to five times a day, preferably one to three times a day.

EXAMPLES

Hereinafter, the present invention is described more concretely by Examples and so on. The present invention is not limited to the following embodiments.

Test Example 1: Verification of Diarrhea Preventing Effect

1. Preparation of Pectin

Pectins 1 to 8 shown in Table 2 were prepared. The pectins have different degrees of esterification and degrees of amidation. The degree of esterification, the degree of amidation, and the degree of free acids of each pectin were measured according to the methods described above.

The weight-average molecular weight of each pectin was determined by using size exclusion chromatography. Concrete measuring conditions for weight-average molecular weight are as follows.

Using Shodex GPC 101 (available from SHOWA DENKO K.K.) to which two TSKgel GMPW$_{XL}$ (available from TOSOH CORPORATION) are connected, a differential refractometer RI-71S (available from SHOWA DENKO K.K.) was attached, and the data was analyzed by using 48011 data station GPC program (System Instruments Co., Ltd.). The molecular weight of the obtained peak was determined according to the calibration curve prepared on the basis of the elution times and the molecular weights of maltotriose and pullulan reference standards (having molecular weights of 504, 1540, 6200, 21700, 48800, 200000, 348000, 2560000). The setting conditions of the size exclusion chromatography are as follows.

Model: Shodex GPC 101 (SHOWA DENKO K.K.)
Detector: Differential refractometer RI-71S (SHOWA DENKO K.K.)
Column: Two connected TSKgel GMPW$_{XL}$, φ7.8 mm×300 mm (TOSOH CORPORATION)
Column temperature: 40° C.
Flow rate: 1.0 ml/min
Mobile phase: 0.1 mol/l sodium nitrate solution
Injection amount of sample liquid: 100 μl 2. Preparation of Nutritional Composition A nutritional composition (liquid form) having a composition shown in Table 1 was prepared. Concretely, after adding the ingredients other than pectin to water and mixing with a mixer, the mixture was adjusted to pH 7.0, and then pectin was added and homogenized (50 MP, 2 passes) with a high-pressure homogenizer (using LAB-1000, available from APV). The homogenized nutritional composition (oil-in-water emulsion composition) was packed in a pouch, and subjected to a heat sterilization treatment (121° C., 10 minutes). Comparative Example 1 is a nutritional composition not containing pectin. The pH of the finally obtained nutritional composition is shown in Table 2.

3. Evaluation of Diarrhea Preventing Effect

For evaluating the diarrhea preventing effect when each nutritional composition was ingested, male SD rats (9 to 10 weeks of age) were allowed to freely ingest a preparation of each nutritional composition for two weeks. Properties of feces of the last five days were observed and recorded. Properties of feces were determined as normal feces or diarrhea (watery feces or caddy feces) by visual observation. In this test, four to five rats were used for each group.

The obtained result is shown in Table 2. The animals fed with a nutritional composition not containing pectin (Comparative Example 1) showed diarrhea, and this result is considered to reflect development of diarrhea that is a complication at the time of administration with an enteral nutrient. While amelioration in diarrhea was not observed with the nutritional compositions respectively containing pectins 1 to 3 (Comparative Examples 2 to 4), normal feces revealing the diarrhea preventing effect was observed with the nutritional compositions respectively pectins 4 to 8 (Examples 1 to 4 and Comparative Example 5).

That is, the result of the present test revealed that development of diarrhea can be effectively suppressed by selecting a pectin having a degree of esterification of 10 to 30%, a degree of amidation 0 to 25%, and a degree of free acids of 64% or more.

TABLE 1

| | Ingredient | Mixing rate (g/L) |
|---|---|---|
| Pectin | Any one of pectins 1 to 8 shown in Table 2 | 6.5 |
| Lipid | Rice oil ("Rice Salad Oil", TSUNO CO., LTD.) | 23 |
| Dietary fiber | Gatti gum ("Gatti gum SD", San-Ei Gen F.F.I., Inc.) | 5 |
| Bivalent metal salt | Tricalcium phosphate ("VERSACAL MP", ORGANO FOODTECH CORPORATION) | 1.7 |
| | Trimagnesium phosphate ("Trimagnesium phosphate", Taihei Chemical Industrial Co., Ltd.) | 1.7 |
| Protein | Enzymatic digest of casein ("TATUA2391", Tatua Japan Company Limited) | 50 |
| Saccharide | Dextrin ("TK-16", Matsutani Chemical Industry Co., Ltd.) | 150 |
| pH adjustor | Sodium hydroxide ("Sodium hydroxide", Kanto Chemical Industry Co., Ltd.) | Appropriate amount (adjusted to pH 7 before introduction of pectin) |
| Water | Purified water | Balance |
| Energy density | | 1000 kcal/L |

TABLE 2

| Nutrient composition | Employed pectin | | | | | pH of nutritional composition | Properties of faces |
|---|---|---|---|---|---|---|---|
| | Structure of pectin | Degree of esterification (%) | Degree of amidation (%) | Degree of free acids (%) | Weight-average molecular weight | | |
| Comparative Example 1 | — | — | — | — | — | 6.7 | Diarrhea |
| Comparative Example 2 | Pectin 1 | 58 | 0 | 42 | 440,000 | 6.1 | Diarrhea |
| Comparative Example 3 | Pectin 2 | 23 | 19 | 58 | 570,000 | 6.5 | Diarrhea |
| Comparative Example 4 | Pectin 3 | 37 | 0 | 63 | 370,000 | 6.1 | Diarrhea |
| Example 1 | Pectin 4 | 15.3 | 20.3 | 64.4 | 400,000 | 6.5 | Normal |
| Example 2 | Pectin 5 | 12.1 | 18.4 | 69.5 | 440,000 | 6.5 | Normal |
| Example 3 | Pectin 6 | 25 | 0 | 75 | 530,000 | 6.5 | Normal |
| Example 4 | Pectin 7 | 20.1 | 0 | 79.9 | 510,000 | 6.4 | Normal |
| Comparative Example 5 | Pectin 8 | 10 | 0 | 90 | 430,000 | 6.6 | Normal |

Test Example 2: Verification of Viscosity Stability

We had the impression that only Comparative Example 5 among the nutritional compositions used in the Test example 1 showed gradual increase in viscosity during the test period. Thus, for Example 2, Example 4 and Comparative Example 5 among the nutritional compositions used in the Test example 1, transition of viscosity during storage at normal temperature was examined.

In the state that the nutritional composition was packed in a pouch after heat sterilization, the nutritional composition was stored at 25° C., and after a lapse of a predetermined period, the nutritional composition was taken out of the pouch, and measured for the viscosity. For measurement of viscosity, a type B viscometer (model RB80L, TOKI SANGYO CO., LTD.) was used, and measurement was carried out at 25° C., at a number of rotations of 12 rpm.

The obtained result is shown in Table 3. While the viscosity was stably kept after the storage in the nutritional compositions of Examples 2 and 4, significant increase in viscosity was observed as early as 7 days after preparation in the nutritional composition of Comparative Example 5.

This test result reveals that the pectin having a degree of esterification of 10 to 30% and a degree of amidation of 0 to 25% contained in the nutritional composition experiences increase in viscosity during storage and cannot provide viscosity stability when the content of free acid is 90%. In an actual case of transnasal enteral administration in the form of an enteral nutrition, a composition having a viscosity of more than 100 mPa·s requires a long time for administration, so that such a composition is considered to be impractical. Therefore, it is necessary to make the degree of free acids of the pectin less than 85% to provide viscosity stability during storage.

These results of Test examples 1 and 2 demonstrated that it is necessary to select a pectin having a degree of esterification of 10 to 30%, a degree of amidation of 0 to 25%, and a degree of free acids of 64% or more and less than 85% so as to provide viscosity stability during storage while effectively preventing diarrhea.

TABLE 3

|  | Viscosity directly after preparation (mPa·s) | Viscosity after 7 days from start of storage (mPa·s) | Viscosity after 14 days from start of storage (mPa·s) |
| --- | --- | --- | --- |
| Example 2 | 10.8 | 15.4 | 16.0 |
| Example 4 | 9.9 | 15.0 | 15.7 |
| Comparative Example 5 | 19.3 | 177.5 | 187.5 |

The invention claimed is:

1. A nutritional composition for preventing diarrhea comprising
    a pectin having a degree of esterification of 10 to 30%, a degree of amidation of 0 to 25%, and a degree of free acids of 64% or more and less than 85%,
    lipid,
    carbohydrate other than the pectin, and
    protein,
    wherein the pectin has a weight-average molecular weight of 350000 to 600000.

2. The nutritional composition for preventing diarrhea according to claim 1, wherein as the carbohydrate, dietary fiber other than the pectin, and/or saccharide is contained.

3. The nutritional composition for preventing diarrhea according to claim 1, wherein as the carbohydrate, gum arabic and/or ghatti gum is contained.

4. The nutritional composition for preventing diarrhea according to claim 1, further comprising a bivalent metal salt.

5. The nutritional composition for preventing diarrhea according to claim 4, wherein the bivalent metal salt is an insoluble salt that releases a bivalent metal ion in an acidic region.

6. The nutritional composition for preventing diarrhea according to claim 1, which is in a liquid form.

7. The nutritional composition for preventing diarrhea according to claim 6, containing 3 to 15 g/L of the pectin.

8. The nutritional composition for preventing diarrhea according to claim 6, having a viscosity at 25° C. of 2 to 100 mPa·s.

9. A method for preventing diarrhea, comprising the step of making a subject in need of preventing diarrhea have administration or ingestion with the nutritional composition for preventing diarrhea according to claim 1.

10. The method for preventing diarrhea according to claim 9, wherein as the carbohydrate, dietary fiber other than the pectin, and/or saccharide is contained.

11. The method for preventing diarrhea according to claim 9, wherein as the carbohydrate, gum arabic and/or ghatti gum is contained.

12. The nutritional composition for preventing diarrhea according to claim 2, wherein as the carbohydrate, gum arabic and/or ghatti gum is contained.

13. The method for preventing diarrhea according to claim 10, wherein as the carbohydrate, gum arabic and/or ghatti gum is contained.

14. The method for preventing diarrhea according to claim 9, wherein the nutritional composition further comprises a bivalent metal salt.

15. The nutritional composition for preventing diarrhea according to claim 2, further comprising a bivalent metal salt.

16. The nutritional composition for preventing diarrhea according to claim 3, further comprising a bivalent metal salt.

17. The nutritional composition for preventing diarrhea according to claim 12, further comprising a bivalent metal salt.

18. The method for preventing diarrhea according to claim 11, wherein the nutritional composition further comprises a bivalent metal salt.

19. The method for preventing diarrhea according to claim 10, wherein the nutritional composition further comprises a bivalent metal salt.

* * * * *